United States Patent [19]

Bournonville et al.

[11] 4,380,673

[45] Apr. 19, 1983

[54] CATALYST AND PROCESS FOR MANUFACTURING A KETONE BY DEHYDROGENATION OF A SECONDARY ALCOHOL

[75] Inventors: Jean-Paul Bournonville, Chatou; Roger Snappe, Sevres; Jean Miquel, Paris; Germain Martino, Poissy, all of France

[73] Assignee: Institut Francais Du Petrole, Rueil-Malmaison, France

[21] Appl. No.: 277,581

[22] Filed: Jun. 26, 1981

[30] Foreign Application Priority Data

Jun. 26, 1980 [FR] France .................................. 80 14290
Jan. 19, 1981 [FR] France .................................. 81 01018

[51] Int. Cl.³ .............................................. C07C 45/00
[52] U.S. Cl. ..................................... 568/361; 568/406; 568/322; 252/466 R
[58] Field of Search ............... 568/403, 406, 361, 465; 252/466 R

[56] References Cited

U.S. PATENT DOCUMENTS

| | | | |
|---|---|---|---|
| 1,961,912 | 6/1934 | Querfurth | 568/403 |
| 2,303,550 | 12/1942 | Houghton et al. | 568/361 |
| 3,047,630 | 7/1962 | Addy | 568/406 |
| 3,554,930 | 1/1971 | Rogers et al. | 568/406 |
| 3,778,477 | 12/1973 | Mueller et al. | 568/403 |
| 3,884,981 | 5/1975 | Kiff | 568/403 |
| 3,981,923 | 9/1976 | Stouthomer et al. | 568/406 |

FOREIGN PATENT DOCUMENTS

998824  7/1965  United Kingdom ................ 568/361

OTHER PUBLICATIONS

Mikholenko et al., vol. 89, #42304v (1978)
Meriaux et al., vol. 89, #163006h (1978)
Ermolenko et al., vol. 83, #9262h (1978)
Masai et al., vol. 83, #130883q (1973)

*Primary Examiner*—James H. Reamer
*Attorney, Agent, or Firm*—Millen & White

[57] ABSTRACT

A secondary alcohol dissolved in a $C_{12}$ to $C_{20}$ paraffinic hydrocarbon substantially free of aromatics and of sulfur is dehydrogenated to the corresponding ketone at a temperature of 170°–230° C. in the presence of a catalyst of the Raney nickel type containing from 0.1 to 10% by weight of an additional metal consisting of copper, silver, gold, tin, lead, zinc, cadmium, indium or germanium, the ketone being preferably removed, as it is formed, from the reaction medium. A catalyst for use in the present process is provided.

17 Claims, 1 Drawing Figure

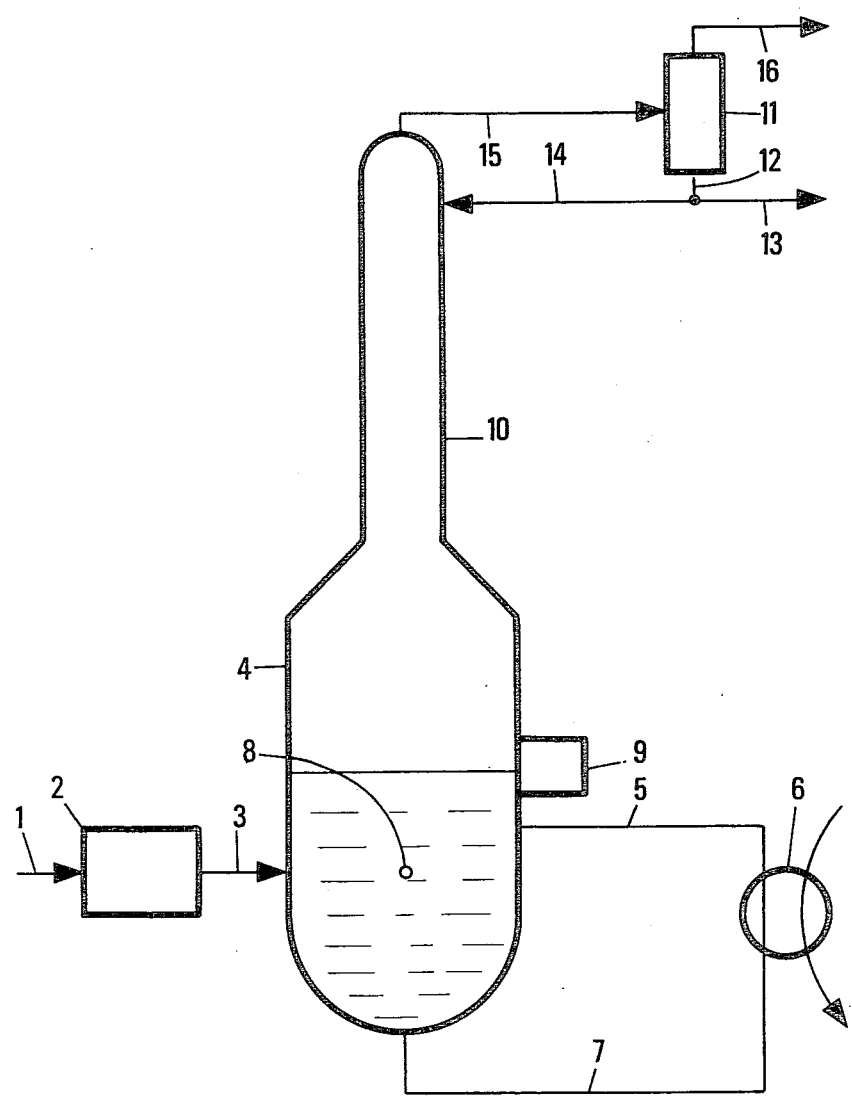

CATALYST AND PROCESS FOR MANUFACTURING A KETONE BY DEHYDROGENATION OF A SECONDARY ALCOHOL

BACKGROUND OF THE INVENTION

The dehydrogenation of isopropanol, 2-butanol and cyclohexanol to acetone, methylethylketone and cyclohexanone respectively may be effected industrially in the vapor phase at a relatively high temperature (300°–550° C.), in the presence of a dehydrogenaton catalyst. This catalyst may contain a heavy metal from one of groups I, II, VI, VII and VIII of the periodic classification of the elements and more particularly such a metal as copper, magnesium, nickel, zinc, etc. these metals having sometimes added thereto other metals or derivatives of metals such as tin and lead, for example. The operating pressure is generally low and often not substantially different from the atmospheric pressure.

The necessity of operating in the vapor phase at a relatively high temperature and low pressure is the main cause of a number of drawbacks:

1. substantial supply of heat at a high thermal level;
2. deactivation of the catalyst by decrease of its active surface owing to the growth of the particles by re-agglomeration;
3. deactivation of the catalyst by "coke" deposit making necessary a regeneration of the catalyst by combustion at about 500° C., by means of an oxygen-nitrogen mixture containing, for example, 2% of oxygen, this regeneration being effected every 10 days in some cases;
4. incomplete conversion of the alcohol which requires a fractionation of the reaction effluent followed with a recycling of the unconverted alcohol;
5. parasitic reactions which decrease the total yield and the purity of the produced hydrogen. These reactions are, for example:
   (a) formation of degradation products such as methane and carbon monoxide;
   (b) dehydration of the alcohol to an olefin or to a cycloolefin which, by condensation with the formed ketone, may result in the formation of products of the diacetone alcohol type and, subsequently of mesityl oxide;
6. the use of an apparatus which is rather impractical in view of the following facts:
   arrangement of the catalyst in furnace tubes where the thermal regulation is not easy,
   periodical disassembling for cleaing or changing the catalyst.

The use of a process wherein the reaction is conducted in the liquid phase makes it possible to avoid most of the above-mentioned drawbacks.

In the prior art, it has been established, on the one hand, that the removal of hydrogen was necessary to displace the equilibrium towards the conversion of alcohol to ketone, thermodynamically unfavoured at low temperature and, on the other hand, that the removal of the ketone from the reaction medium, as it is formed, facilitates the obtention of a satisfactory reaction velocity. The second condition is satisfied by adding to the reaction medium certain solvents which do not react under the operating conditions and make it possible to conduct the reaction at a temperature higher than the boiling temperature of the ketone, under the prevailing pressure.

In the prior art, solvents have been selected particularly with the following characteristics of:
having a high boiling point, higher than the boiling point of the alcohol to be converted;
being not subject to any conversion or degradation in the reaction medium;
having a much lower adsorption coefficient on the catalyst than that of the alcohol to be converted.

The following compounds could thus be used as solvents: heavy naphthenic hydrocarbons such as decahydronaphthalene, heavy paraffinic hydrocarbons, naphthenic hydrocarbons having at least one paraffinic chain such as hexadecyldecahydronaphthalene or mixtures of the preceding hydrocarbons as they can be found in heavy petroleum cuts.

However, such a process in the liquid phase is finally very disadvantageous as compared with the conventional gaseous phase process. As a matter of fact, in the liquid phase process, the reaction temperature scarcely exceeds 150° C. and, consequently, the conversion is much lower than that obtained in the gaseous phase process at 400° C.: the conversion is about 25% for the manufacture of acetone and about 10% for that of methylethylketone, thus requiring a very substantial recycling of the unconverted alcohol. Moreover, even at 150° C., it is impossible to completely avoid a stripping of the solvent, so that an oversizing of the fractionation stage is required. The occurrence of parasitic hydrogenolysis reactions which produce light hydrocarbons such as methane, ethane, propane and butane do not allow the liquid phase process to attain a selectivity of 100%: the purity of the produced hydrogen is about 98% at a temperature close to 150° C. The temperature increase which favours the hydrogenolysis reactions and the solvent evaporation does not seem to be a good solution.

SUMMARY OF THE INVENTION

It has now been discovered that it is possible to proceed at a sufficiently high temperature, in the liquid phase, by making use of solvents of a particular type, less volatile than those previously used, and provided also that particular catalysts are used whereby a sufficient activity is obtained while limiting the hydrogenolyzing activity. In the present process, a secondary alcohol dissolved in a $C_{12}$ to $C_{20}$ paraffinic hydrocarbon substantially free of aromatics and of sulfur is dehydrogenated to the corresponding ketone at a temperature of 170°–230° C. in the presence of a catalyst of the Raney nickel type containing from 0.1 to 10% by weight of an additional metal consisting of copper, silver, gold, tin, lead, zinc, cadmium, indium or germanium, the ketone being preferably removed, as it is formed, from the reaction medium. A catalyst for use in the present process is provided.

BRIEF DESCRIPTION OF THE DRAWING

The FIGURE shows, diagrammatically, an apparatus suitable for effecting the process of the invention.

DETAILED DISCUSSION

The solvent conforming with the invention consists essentially of at least one paraffinic hydrocarbon containing 12 to 20 carbon atoms per molecule. Preferably there is used a mixture of paraffinic hydrocarbons, for example any heavy saturated cut, preferably having an initial boiling point higher than 240° C. under atmospheric pressure (0.1 MPa). This solvent must contain substantially no cycloparaffinic or cycloolefinic hydrocarbon. As a general rule, the content of the solvent in aromatic hydrocarbons or aromatic hydrocarbon generators, under the operating conditions of the reaction must be lower than 1000 p.p.m. (expressed as benzene) and preferably lower than 300 p.p.m. Similarly the sulfur content must remain lower than 500 p.p.m. and, preferably lower than 200 p.p.m.

Contents of aromatic hydrocarbons or aromatic hydrocarbon generators and of sulfur higher than those determined in the specifications are not detrimental to the hydrogen purity (since they also inhibit the hydrogenolysis reaction) but result in a substantial decrease of the conversion rate. The "aromatic hydrocarbon generators" are essentially cycloparaffins and cycloolefins.

The reaction is conducted under a pressure generally close to the atmospheric pressure, at a temperature from about 170° to 230° C., but preferably from 180° to 220° C. and, more particularly, from 185° to 210° C. The adoption of this type of solvent and the temperature increase thus makes it possible to obtain a conversion rate increased by 20 to 40% as compared to a process conducted only at about 150° C.

However, it is known that the temperature increase results in a noticeable increase of the hydrogenolysis and, consequently, in a decrease of the purity of the produced hydrogen. The use of a conveniently selected catalyst will make it possible to avoid these disadvantages and to provide for a hydrogen molar purity from 97.5 to 98%.

The catalyst used according to this invention is of the Raney nickel type, i.e., it contains Raney nickel or any other compound equivalent to Raney nickel where the nickel is replaced, at least partly, by a conventional dehydrogenating metal pertaining generally to group VIII of the periodic classification of elements, for example cobalt, platinum, rhodium, etc.

However, according to a first embodiment of the invention, it is compulsory to add to this catalyst of the Raney nickel type at least one additional metal or compound of an additional metal selected from the group consisting of copper, silver, gold, tin, germanium, lead, zinc, cadmium and indium. This additional metal produces a substantial decrease of the hydrogenolysis parasitic reaction.

The additional metal may be added during the preparation of the Raney type alloy or a compound of the selected metal soluble in the liquid phase containing the Raney nickel type alloy can be added directly to the already prepared Raney nickel type alloy, suspended in a liquid.

The amount of additional metal to be added is generally from 0.1 to 10% by weight (expressed as elemental metal) and, preferably, from 0.2 to 6% by weight with respect to the material of the Raney nickel type. There is thus obtained a catalyst containing the indicated amounted (0.1 to 10% or better 0.2 to 6% by weight) of additional metal.

The decrease of the hydrogenolizing activity results in a substantial increase of the selecitivity, by producing hydrogen of sufficient purity since it contains only small amounts of light hydrocarbons, hydrogenolysis products (methane, ethane, etc.) and also the life time of the catalyst is much longer.

However it has also been found, and this constitutes a, preferred, embodiment technique of the invention, that it is very advantageous to introduce the one or more additional metals not as above indicated but by another method consisting of injecting them in solution into the reaction zone, at the reaction temperature, the catalyst of the Raney nickel type, suspended in the reaction solvent, having been introduced into the reaction zone earlier. A method of introducing the one or more additional metals consists in introducing the one or more compounds of these metals in solution in the reaction solvent in sufficient amount to obtain the desired content of additional metal.

Then begins the introduction of the feed charge, i.e. of the secondary alcohol. Another method, generally preferred, consists of introducing the one or more additional metal(s) in solution in the secondary alcohol or in a portion thereof in sufficient amount to obtain the desired content of additional metal. The addition of the additional metal (in conformity with said second technique) is thus conducted by injection into the reaction medium of a solution of at least one compound of a metal which will be arbitrarily called an organometallic compound of said additional metal. It is thus required:

(a) that the solubility of the one or more organometallic compounds in the reaction medium and/or the solvent be sufficient for making it possible to add the amount of additional metal necessary for obtaining a high conversion rate and a high hydrogen purity, (b) that the reactivity of these organometallic compounds with the alcohol to be dehydrogenated be substantially nil.

The one or more organometallic compounds used for the preparation of the catalyst are preferably selected from the group consisting of:

(a) alkylmetals of said additional metals, whose alkyl radical has paraffinic or cycloparaffinic structure and contains from 1 to 10 carbon atoms but preferably from 3 to 6 carbon atoms per molecule. Examples are: diethylcadmium, dibutylcadmium, dimethylcadmium, diethylzinc, dibutylzinc, trimethylindium, tetrapropylgermanium, tetrabutylgermanium, tetrabutyltin, dimethylethylpropyltin, dimethyldiethyltin, tetramethyllead, tetraethyllead, ethylsilver;

(b) the arylmetals of said additional metals. Examples are: diphenyltin, diphenylgermanium, triphenylbenzyllead, tetraphenyllead, diphenylzinc, triphenylindium;

(c) the alkylaryl metals or arylalkyl metals of the additional metals where the alkyl radical is defined as in (a). Examples are: diethyldiphenyltin, diethyldiphenylgermanium, diethylphenylindium, methylphenylzinc, tetrabenzyltin, and tetrabenzylgermanium;

(d) the acetylacetonates of said additional metals. Examples are: copper acetylactonate, cadmium acetylacetonate, zinc acetylacetonate, indium acetylacetonate;

(e) the metals salts of said additional metals with organic acids whose hydrocarbon chain contains from 1 to 6 carbon atoms and more particularly from 1 to 4 carbon atoms per molecule. Examples are: copper acetate, formate and butyrate, silver acetate, zinc acetate, tin acetate, lead acetate, gold acetate, compounds soluble in the considered alcohol at the used concentrations.

The metal amount to be added is generally from 0.1 to 10% and, more particularly, from 0.3 to 5% by weight (expressed as elemental metal), preferably from 0.5 to 4% by weight, with respect to the material of the Raney nickel type. Consequently, the addition to the reaction medium, at the beginning of the reaction, of one or more organometallic compounds of additional metals will be continued until the selected content has been obtained. (The percent of additional metal on the catalyst may be determined at the end of the reaction when recovering the used catalyst; a sampling from the reaction medium makes it possible to check the absence of any detectable amount of additional metal in the liquid medium).

One of the advantages of the injection of an organometallic compound in solution in the solvent and/or in the alcohol charge (second technique) as compared to the use of a Raney type alloy with an additional metal (first technique) is that generally the total amount of additional metal required to be deposited on the particles of the catalyst mass is not as high as the total amount of additional metal which has to be introduced into the catalyst mass in conformity with the first technique of the invention. This might be explained eventually by an action of the additional metal directly at the level of the catalyst surface. Thus, any additional metal added would participate in the improvement of the catalyst performance whereas, in the case of addition to a Raney type alloy of the additional metal, in conformity with the first technique, only a fraction of said additional metal would act at the level of the active catalyst surface, the other portion remaining as alloy with nickel in the mass of the catalyst particles.

It is sometimes preferable, in the case of the second technique, to proceed in the presence of hydrogen when adding the additional metal in view of the formation of by-products which result:

(a) from the reaction of the organometallic compounds with the Raney nickel and then
(b) from their further decomposition. The available hydrogen thus provides for the release of the hydrocarbon radicals which, after recombination with the available hydrogen, lead, among others, to hydrocarbons easily removed by distillation under the operating conditions of the unit. The hydrogen required for the removal of the by-products is advantageously the hydrogen produced during the dehydrogenation of the secondary alcohol. This explains why, preferably, the additional metal compound is introduced in solution in the alcohol to be hydrogenated.

However, the injection of the organometallic compound of the additional metal may be effected, not in solution in the charge of alcohol to be dehydrogenated, but directly in the reaction solvent containing the catalyst of the Raney nickel type. It is advantageous to introduce simultaneously hydrogen produced from any convenient source, in order to effect the fixation of the additional metal on the catalyst of the Raney nickel type in the presence of hydrogen. The hydrogen may be injected at a flow rate from 0.5 to 2 liters per hour and per gram of catalyst of the Raney nickel type.

The use of the catalyst conforming with said second technique will result in a decrease of the hydrogenolyzing activity and hence in a selectivity increase (decrease of the amount of degradation products formed).

The process according to the invention (with the use of the first or of the second technique) is applicable to the manufacture of any ketone whose boiling point, at atmospheric pressure (about 0.1 MPa), is lower than the selected reaction temperature, this maximum temperature being about 220° C. or 230° C. Briefly stated, the reaction temperature is from 170° to 230° C.; when proceeding in conformity with the second technique, it is preferred to operate at a temperature from 195° to 210° C.

The preparation, according to the invention, of ketones from secondary alcohols, in the liquid phase, is preferably performed with removal, by distillation, of the produced ketone as it is formed; this removal is effected in any convenient apparatus but, preferably, with the apparatus diagrammatically shown in the accompanying drawing.

The secondary alcohol, which it is desired to convert to ketone, is introduced into the reactor 4 through line 1, pumping system 2 and line 3. This reactor 4 contains the solvent and the catalyst. The reactor 4 is provided with a stirring system, diagrammatically shown at 5, 6 and 7, a device 8 for measuring the temperature and a level regulator 9. The heating takes place in exchanger 6.

The reactor 4 contains at its upper part or is overtopped with a fractionation device 10 whose efficiency is responsible for the purity of the obtained product. The vapors of the produced ketone reaching the top of the column are directed through line 15 and are condensed in condenser 11. The condensate is withdrawn through line 12. A portion of the condensate is recovered through line 13 and another portion is fed to the top of the fractionation column 10 through line 14 so as to adjust the reflux rate. From line 16, there is recovered a gaseous fraction of high hydrogen content.

The following non-limitative examples illustrate the invention; in the following, "conversion" means the conversion to butanone (examples 2 to 12) or to acetone (example 13).

EXAMPLE 1

A catalyst is prepared according to the first technique of the invention by introducing into a vessel, provided with a stirrer, 2 liters of water and then 500 g of Raney alloy containing 50% by weight of aluminum, 47.5% by weight of nickel and 2.5% by weight of copper. There is then added progressively, in three hours, 1 liter of an aqueous solution containing 750 g per liter of sodium hydroxide, while taking care to maintain the temperature at about 70° C. After 1 hour of additional stirring, the mixture is allowed to settle, the aqueous phase is separated and the solid washed four times with water at ordinary temperature and the catalyst, containing 5% by weight of copper, is then ready for use. For manufacturing catalysts containing, for example, gold, silver, germanium or tin, it suffices to replace copper by the desired amount of the selected metal.

EXAMPLE 2

This example concerns the manufacture of methylethylketone from 2-butanol.

The solvent used is a solvent A defined as follows:

The solvent a consists essentially of normal paraffinic hydrocarbons having 12 to 16 carbon atoms per molecule and exhibiting the following characteristics:

| | |
|---|---|
| $d_4^{15}$ | 0.774 |
| distillation IP | 250° C. |
| 50% | 270° C. |
| FP | 300° C. |
| aromatic hydrocarbons (and generators) | 150 ppm |

-continued

| | |
|---|---|
| total sulfur | 100 ppm |

The apparatus consists of a reactor of a 2 liters capacity provided with an efficient stirring system, a regulating and temperature control system and a fractionation and separation system in conformity with the FIGURE.

The obtained gas and liquids are measured and analyzed by gas phase chromatography.

The reactor contains a solvent A selected for conducting the reaction in the liquid phase at the desired temperature and for maintaining the catalyst in suspension in the reaction medium. The charge to be converted is introduced into the reactor through a proportioning pump.

2-Butanol (d=0.808) is injected into the reactor where solvent A is present with the catalyst maintained in suspension by efficient stirring; the reaction temperature is 190° C. The 2-butanol is introduced at a pph=38 kg of charge per kg of catalyst and per hour. The catalyst used is Raney nickel containing 5% by weight of copper and prepred as indicated in example 1.

The (instantaneous) molar conversion rates obtained after 1.5 and 5 hours of run are respectively 43.2% and 43.5% and the molar purity of the obtained hydrogen is 97.9 and 97.6%.

Now with a catalyst containing 0.15% of copper, the hydrogen purity after 1.5 and 5 hours is, respectively, 95.5% and 95.3%. With a catalyst containing 0.25% of copper, the hydrogen purity after 1.5 and 5 hours, respectively, reaches 97.1 and 96.9%.

EXAMPLE 3 (comparative)

Example 2 is repeated under the same conditions, except that the catalyst is replaced with Raney nickel without additive, i.e. without copper.

After 1.5 and 5 hours of run, respectively, the molar conversion (instantaneous) is 43.6% and 43.5%, but the molar purity of the obtained hydrogen is only 89.2% and 89.1%.

The comparison of examples 2 and 3 makes obvious the inhibiting effect on the hydrogenolyzing activity due to the addition of the specified amount of copper to Raney nickel.

EXAMPLE 4 (comparative)

Example 2 is repeated but with the use of a solvent B not conforming with the invention.

The solvent B has the following composition:

| | |
|---|---|
| Paraffins (12 to 16 carbon atoms per molecule) | 57% by weight |
| Cycloparaffins | 40% by weight |
| Aromatics | 2.9% by weight |
| Olefins | 0.1% by weight |

Its characteristics are as follows:

| | | |
|---|---|---|
| $d_4^{15}$ | | 0.815 |
| distillation | IP | 271° C. |
| | 50% | 283° C. |
| | FP | 303.5° C. |
| total sulfur | | 50 ppm |

The molar conversions obtained after 1.5 hour and 5 hours or run are, respectively, 26.4% and 19.2%.

The molar purity of the obtained hydrogen is, respectively, 90.5 and 91.8%.

These results demonstrate the advantage of avoiding the use of solvents containing other hydrocarbons than paraffins.

EXAMPLE 5

Example 2 is repeated with the use of catalysts wherein copper has been replaced by a metal which is successively tin, germanium, silver and gold.

The nature of the catalysts and the obtained results are reported in Table I.

TABLE I

| METAL | MOLAR CONVERSION AFTER: | | $H_2$ PURITY AFTER: | |
|---|---|---|---|---|
| (% by weight) | 1.5 h | 5 h | 1.5 h | 5 h |
| 5% Cu | 43.2 | 43.5 | 97.9 | 97.6 |
| 5% Sn | 42.6 | 42.7 | 98.2 | 98.1 |
| 5% Ge | 42.8 | 42.5 | 98.3 | 98.3 |
| 2.5% Ag | 43.1 | 43.6 | 98.0 | 97.8 |
| 2.5% Au | 43.4 | 43.4 | 97.9 | 98.0 |

EXAMPLE 6

Example 2 is repeated by using various solvents $A_1$ to $A_4$ similar to solvent A but differing by the aromatic hydrocarbons and sulfur contents.

Table II summarizes the obtained results.

TABLE II

| SOLVENT | A | $A_1$ | $A_2$ | $A_3$ | $A_4$ |
|---|---|---|---|---|---|
| Aromatic hydrocarbons ppm | 150 | 280 | 380 | 950 | 1100 |
| Sulfur ppm | 100 | 180 | 220 | 450 | 550 |
| Molar conversion after 1.5 hours | 43.2 | 43.1 | 41.6 | 40.1 | 37.2 |
| Molar conversion after 5 hours | 43.5 | 43.4 | 42.1 | 38.5 | 34.1 |
| Purity of the obtained hydrogen (molar) after 1.5 hours | 97.9 | 97.9 | 98.0 | 98.1 | 98.1 |
| Purity of the obtained hydrogen (molar) after 5 hours | 97.6 | 97.6 | 97.7 | 97.7 | 97.8 |

EXAMPLE 7

Example 1 is repeated at various temperatures.
The results are summarized in Table III.

TABLE III

| TEMPERATURE (°C.) | 240 | 220 | 190 | 180 | 175 | 150 |
|---|---|---|---|---|---|---|
| Molar conversion after 1.5 hours | 35.8 | 42.7 | 43.2 | 42.6 | 40.9 | 31.5 |
| Purity of the obtained hydrogen (molar) after 1.5 hours | 97.9 | 97.9 | 97.9 | 97.9 | 97.9 | 98.0 |

It is observed, as seen from the comparative tests of Tables II and III that, when operating at other temperatures or with another solvent than those conforming to the invention that the purity of the produced hydrogen may be slightly higher than that obtained when proceeding in conformity with the invention, but, in such a case, the conversion rate is substantially lower than that obtained when operating in conformity with the invention.

It is also shown (example 3) that, by omitting the additional metal, the conversion rate may be slightly greater than with the use of an additional metal. But this is at the sacrifice of the hydrogen purity.

The interest of the invention is to obtain simultaneously, by a critical selection of several parameters, a satisfactory conversion and a convenient purity of the produced hydrogen, hence a convenient selectivity.

EXAMPLE 8

This example concerns the manufacture of methylethylketone from 2-butanol ($d_4^{20} = 0.808$) by operating in conformity with said second technique.

The solvent is the solvent A as defined in example 2. The apparatus used is that of example 2.

The obtained products are measured and analyzed by gas phase chromatography.

An efficient stirring is necessary to conduct the reaction in the liquid phase and maintain the catalyst suspended in the reaction medium.

After stabilization of the temperature of the reaction zone (containing solvent and suspended Raney nickel: the starting Raney alloy used here was formed of 52% by weight of aluminum and 48% by weight of nickel) at the selected reaction temperature, there is injected a solution containing the alcohol to be dehydrogenated and the organometallic compound in the convenient proportions for obtaining the desired content of additional metal.

Table IV reports the results obtained after 5 hours of injection of 2-butanol for various amounts of tetrabutyltin injected as a 10% by volume solution in the secondary alcohol. Zero time is arbitrarily considered as being the end of the injection of the tetrabutyltin alcoholic solution and corresponds to the beginning of the injection of the pure alcohol. The operating conditions are as follows: temperature 180° C., pph=8 kg/kg of catalyst/hour and the pressure is close to the atmospheric pressure. The amount of Raney type nickel involved is 10 g. The yield of acetone with respect to the converted alcohol is in all cases higher than 99.5%.

It appears that the addition of the tin results in a slight decrease of the conversion rate. However, this slight decrease of the conversion rate is compensated by a noticeable increase of the selectivity, as shown by the molar purity of the formed hydrogen. However, the interest of the invention is in particular to obtain simultaneously, by a critical selection of several parameters, a satisfactory conversion and a convenient purity of the produced hydrogen, hence a satisfactory selectivity.

TABLE IV

| CATALYST | MOLAR CONVERSION (%) | MOLAR PURITY OF THE HYDROGEN (%) |
|---|---|---|
| Raney nickel alone | 44.6 | 90.4 |
| + 0.34% Sn | 43.4 | 94.1 |
| + 0.68% Sn | 42.4 | 96.0 |
| + 1.36% Sn | 41.4 | 97.6 |
| + 2.04% Sn | 41.2 | 98.5 |
| + 2.72% Sn | 40.5 | 99.1 |
| + 6.50% Sn | 31.0 | 98.7 |
| + 10.0% Sn | 14.0 | 99.0 |

(% Sn with respect to the catalyst mass)

EXAMPLE 9

Example 8 is repeated at different temperatures. Two catalysts are compared: Raney nickel alone and Raney nickel with the addition of 2.72% of tin in accordance with the technique of example 8. The results are reported in Table V. The operating conditions are slightly different from those of examples 2 and 3; the results obtained here, with Raney free of additional metal, are substantially equivalent to those of example 3.

It is observed that above about 200° C., the inhibiting action of tin is higher: consequently, the selectivity is improved as a result of the decrease in the production of light hydrocarbons (methane, ethane, propane and butane) with a corresponding increase of the production of methylethylketone. The ketone yield, in every case, with respect to the converted alcohol, is higher than 99.5%.

TABLE V

| TEMPERATURE (°C.) | RANEY NICKEL | | RANEY NICKEL + 2.7% Sn | |
|---|---|---|---|---|
| | CONVERSION (%) | PURITY $H_2$ (%) | CONVERSION (%) | PURITY $H_2$ (%) |
| 160 | 30 | 97 | 28 | 99.7 |
| 180 | 44 | 90.5 | 41 | 99.0 |
| 200 | 57 | 83.3 | 53 | 97.1 |
| 210 | 64 | 79.0 | 59 | 96.0 |

(% Sn with respect to the catalyst mass).

EXAMPLE 10

Example 8 is repeated with the use of catalysts of the Raney nickel type to which is added an additional metal which is successively copper, silver, gold, germanium, lead, indium and zinc. The results are summarized in Table VI. The addition of organometallic compounds thus maintains a high activity and improves the selectivity (in the case of use of silver and gold acetates, which are insoluble in the solvent, these acetates are introduced as a solution in the alcohol). The ketone yield, in every case, with respect to the converted alcohol, is higher than 99.5%.

TABLE VI

| ADDITIONAL METAL | | | MOLAR CONVERSION (%) | HYDROGEN PURITY (%) |
|---|---|---|---|---|
| NATURE | COMPOUND | % by weight | | |
| Copper | Acetylacetonate | 2.5 | 40.8 | 98.9 |
| Silver | Acetate | 2.5 | 40.2 | 98.7 |
| Gold | Acetate | 4.5 | 39.9 | 98.5 |
| Germanium | Tetrabutyl | 1.7 | 40.5 | 99.0 |
| Lead | Tetraethyl | 4.7 | 40.0 | 98.9 |
| Zinc | Acetylacetonate | 1.5 | 40.7 | 98.8 |
| Indium | Trimethyl | 2.6 | 41.0 | 98.6 |

(% by weight of metal with respect to the catalyst mass).

EXAMPLE 11

The operation is conducted under the same conditions as in example 8, except that the organometallic compound is introduced in the reaction zone as a solution in the reaction solvent and the desired amount of additional metal is thus introduced before starting the introduction of 2-butanol (2.72% of tin have thus been introduced in the catalyst mass).

The obtained conversion rate is 39.4% and the molar purity of the hydrogen is 96.7%. It is recalled that, in example 8, for a 2.72% tin content of the catalyst, there was obtained a conversion rate of 40.5% and a molar hydrogen purity of 99.1%.

This operating manner to inject the organometallic additive thus leads to a conversion and a hydrogen purity lower than those obtained after injection of the organometallic compound in alcoholic medium. This technique thus offers interest only to the extent that it is desired essentially to avoid any interaction between the alcohol to be dehydrogenated and the organometallic compound.

EXAMPLE 12

Example 8 is repeated with catalyst C on which, according to the second technique of the present invention, there was deposited 2.50% by weight of tin. But the process is also conducted in accordance with the first technique with two catalysts $C_1$ and $C_2$ of the Raney nickel type to which were incorporated, during the preparation of the alloy, respectively 6.50% and 2.50% of the tin by weight.

Table VII gives the results obtained with the three tested catalysts. It will be observed that catalysts $C_1$ and $C_2$ require a 6.5% content of tin to obtain results similar to those achieved by means of catalyst C whose tin content is only 2.5%. With catalyst $C_2$ the tin content of 2.5% is still slightly insufficient to obtain an excellent hydrogen purity. The ketone yields with respect to the converted alcohol are respectively (with catalysts $C_1$, $C_2$ and C) of 95%, 98.5% and 99.5%.

TABLE VII

| TEMPERATURE (°C.) | CATALYST $C_1$ (6.5% Sn) | | CATALYST $C_2$ (2.5% Sn) | | CATALYST C (2.5% Sn) | |
|---|---|---|---|---|---|---|
| | CONVERSION RATE (%) | $H_2$ PURITY (%) | CONVERSION RATE (%) | $H_2$ PURITY (%) | CONVERSION RATE (%) | $H_2$ PURITY (%) |
| 180 | 42 | 97.9 | 43.2 | 94.1 | 41 | 99.0 |
| 190 | 42.6 | 97.9 | 46.2 | 92.0 | 46.5 | 98.0 |
| 200 | 42.3 | 97.8 | 50.1 | 90.1 | 52.7 | 97.6 |
| 210 | 42.5 | 97.7 | 56.2 | 88.0 | 58.5 | 97.1 |

The advantage of using a catalyst conforming with the second technique as compared with the catalyst prepared from an alloy to which tin was previously added (first technique) is more substantial at a temperature which, in this case, is close to 200°–210° C.

EXAMPLE 13

This example concerns the manufacture of acetone under operating conditions identical to those of example 8, except that isopropanol is substituted for 2-butanol. The Raney nickel type catalyst contains 2.9% by weight of tin according to the process of example 8.

The conversion rate after 5 hours is 35% (ketone yield: 99.5%) and the molar purity of the produced hydrogen is higher than 99%. Under the same conditions, Raney nickel alone (without tin) provides for a conversion rate of 38.5% (ketone yield: 97%) but with a hydrogen purity of 90.6%. The tin addition thus appears to make the catalyst more selective.

What is claimed is:

1. In a process comprising contacting a secondary alcohol, in the liquid phase and in the presence of a solvent, with a dehydrogenation catalyst, and recovering the resultant ketone, the improvement wherein said catalyst consists essentially of a Raney nickel catalyst and 0.1–10% by weight, expressed as elemental metal and with respect to the Raney nickel, of at least one additional metal, said additional metal being copper, silver, gold, tin, lead, zinc, cadmium, indium or germanium; wherein the reaction is effected at a temperature of about 170°–230° C.; and wherein said solvent is a $C_{12-20}$ paraffinic hydrocarbon or hydrocarbon cut having a content of aromatic hydrocarbons and aromatic hydrocarbon generators, expressed as benzene, lower than 1,000 ppm and a sulfur content lower than 500 ppm; whereby hydrogenolysis to produce degradation products is reduced and the selectivity of the dehydrogenation is increased.

2. A process according to claim 1, wherein said catalyst is prepared by a process comprising the steps of introducing a solution of a compound of said additional metal into a reaction zone containing said Raney nickel catalyst suspended in said solvent, the catalyst suspension being previously heated to the reaction temperature, the amount of said compound of said additional metal introduced being sufficient to incorporate 0.2–6% by weight, expressed as elemental metal and with respect to the Raney nickel, of said additional metal.

3. A process according to claim 1, wherein said secondary alcohol is isopropanol, 2-butanol or cyclohexanol, the resultant ketone being acetone, 2-butanone or cyclohexanone, respectively.

4. A catalyst suitable for catalyzing the dehydrogenation of secondary alcohols to ketones, consisting essentially of Raney nickel and 0.1–10% by weight, expressed as elemental metal and with respect to the Raney nickel, of at least one additional metal, said additional metal being copper, silver, gold, tin, lead, zinc, cadmium, indium or germanium.

5. A catalyst according to claim 4, wherein said additional metal is tin.

6. A catalyst according to claim 5, wherein the amount of said additional metal is 0.2–6% by weight.

7. A process according to claim 1 wherein the temperature is from 185° to 210° C.

8. A process according to claim 1, wherein th solvent contains at most 300 ppm (expressed as benzene) of aromatic hydrocarbons or aromatic hydrocarbon generators and at most 200 ppm of sulfur.

9. A process according to claim 1, wherein the catalyst contains from 0.2 to 6% by weight of additional metal.

10. A process according to claim 1, wherein the resultant ketone is removed, by distillation, from the reaction medium as it is formed.

11. A process according to claim 2, wherein the reaction temperature of the secondary alcohol dehydrogenation is from 195° C. to 210° C.

12. A process according to claim 2, wherein said compound of said additional metal is:
(a) a metal alkyl of said additional metal whose alkyl radical has a paraffinic or cycloparaffinic structure and contains from 1 to 10 carbon atoms per molecule;
(b) a metal aryl of said additional metal;
(c) a metal alkylaryl or arylalkyl of said additional metal, where the alkyl radical is as defined in (a);
(d) an acetylacetonate of said additional metal; or
(e) a metal salt of said additional metal with an organic acid containing from 1 to 6 carbon atoms per molecule.

13. A process according to claim 2, wherein said metal compound is introduced in solution in said reaction solvent before the beginning of the introduction of the secondary alcohol.

14. A process according to claim 13, wherein hydrogen is introduced concurrently with the metal compound, at a flow rate of from 0.5 to 2 liters per hour and per gram of said Raney nickel catalyst.

15. A process according to claim 2, wherein the introduction of said compound of said additional metal is effected concurrently with the introduction of the secondary alcohol in the reaction zone, said compound being introduced as a solution in the secondary alcohol.

16. A process according to claim 2, wherein the content by weight of said additional metal is from 0.5 to 4%.

17. A process according to claim 2, wherein said additional metal is tin.

* * * * *